United States Patent [19]

Yau

[11] Patent Number: 4,876,882
[45] Date of Patent: Oct. 31, 1989

[54] VISCOSITY DETECTION METHOD FOR LIQUID CHROMATOGRAPHY SYSTEMS WITH CARRIER LIQUIDS HAVING TIME-VARYING VISCOSITY

[75] Inventor: Wallace W. Yau, Wilmington, Del.

[73] Assignee: E. I. Du Pont de Nemours and Company, Wilmington, Del.

[21] Appl. No.: 302,899

[22] Filed: Jan. 30, 1989

[51] Int. Cl.⁴ ............................................. G01N 11/08
[52] U.S. Cl. ..................................... 73/55; 73/61.1 C
[58] Field of Search ............................... 73/55, 61.1 C

[56] References Cited

U.S. PATENT DOCUMENTS 4,463,598  8/1984  Haney ........................... 73/61.1 C X
4,578,990  4/1986  Abbott et al. ................ 73/61.1 C X
4,627,271  12/1986  Abbott et al. ............... 73/61.1 C X
4,793,174  12/1988  Yau ......................................... 73/55

Primary Examiner—Stewart J. Levy
Assistant Examiner—Joseph W. Roskos

[57] ABSTRACT

A method for measuring the inherent viscosity of individual solute components in a multicomponent sample in solution with a solvent comprising for each component (1) measuring pressure differences for solvent and for solvent with solute component, as a function of time across two capillary tubes in fluid communication (2) measuring concentrations of component as a function of time, and (3) obtaining inherent viscosity by means of a described mathematical relationship.

1 Claim, 4 Drawing Sheets

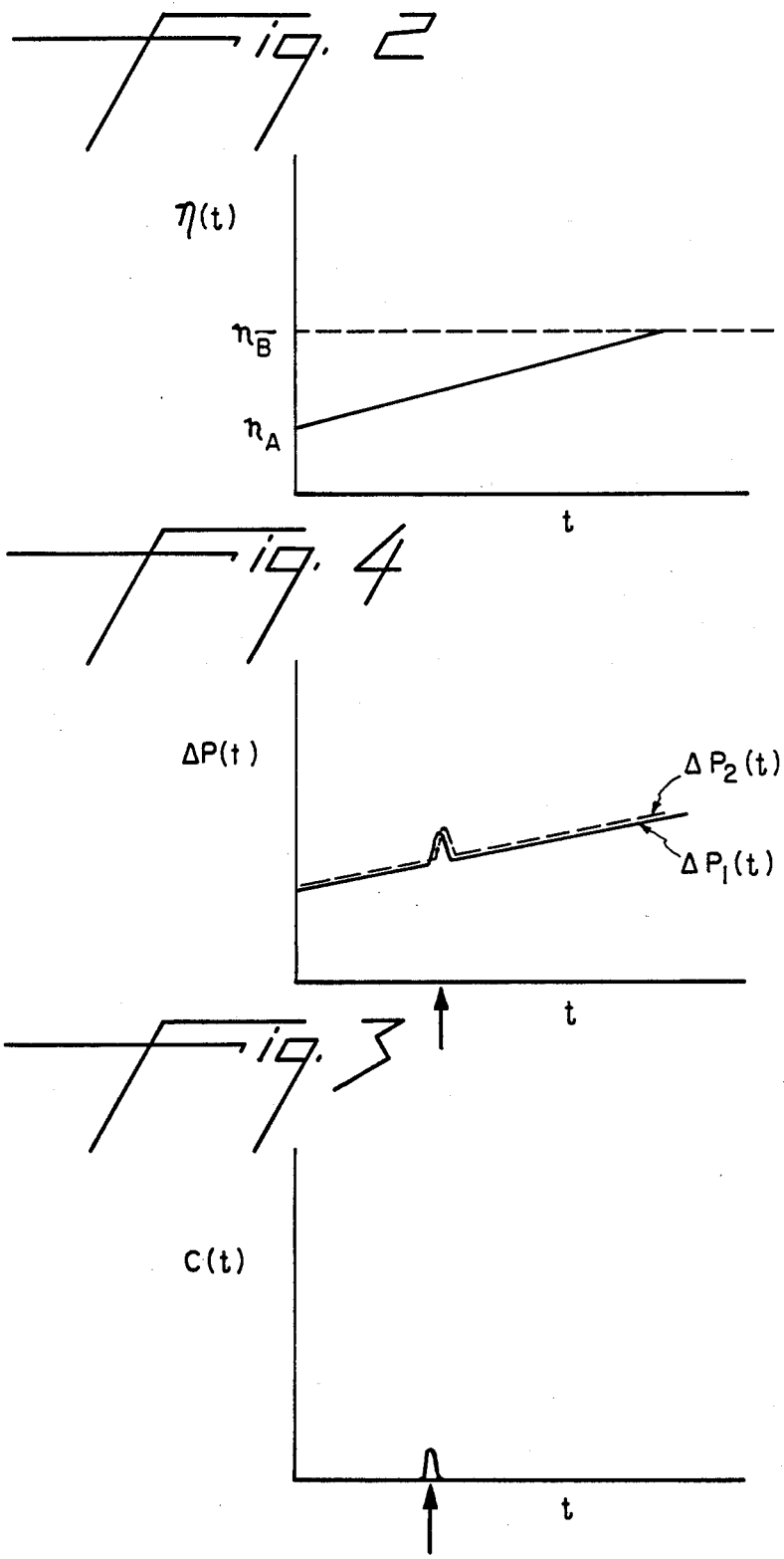

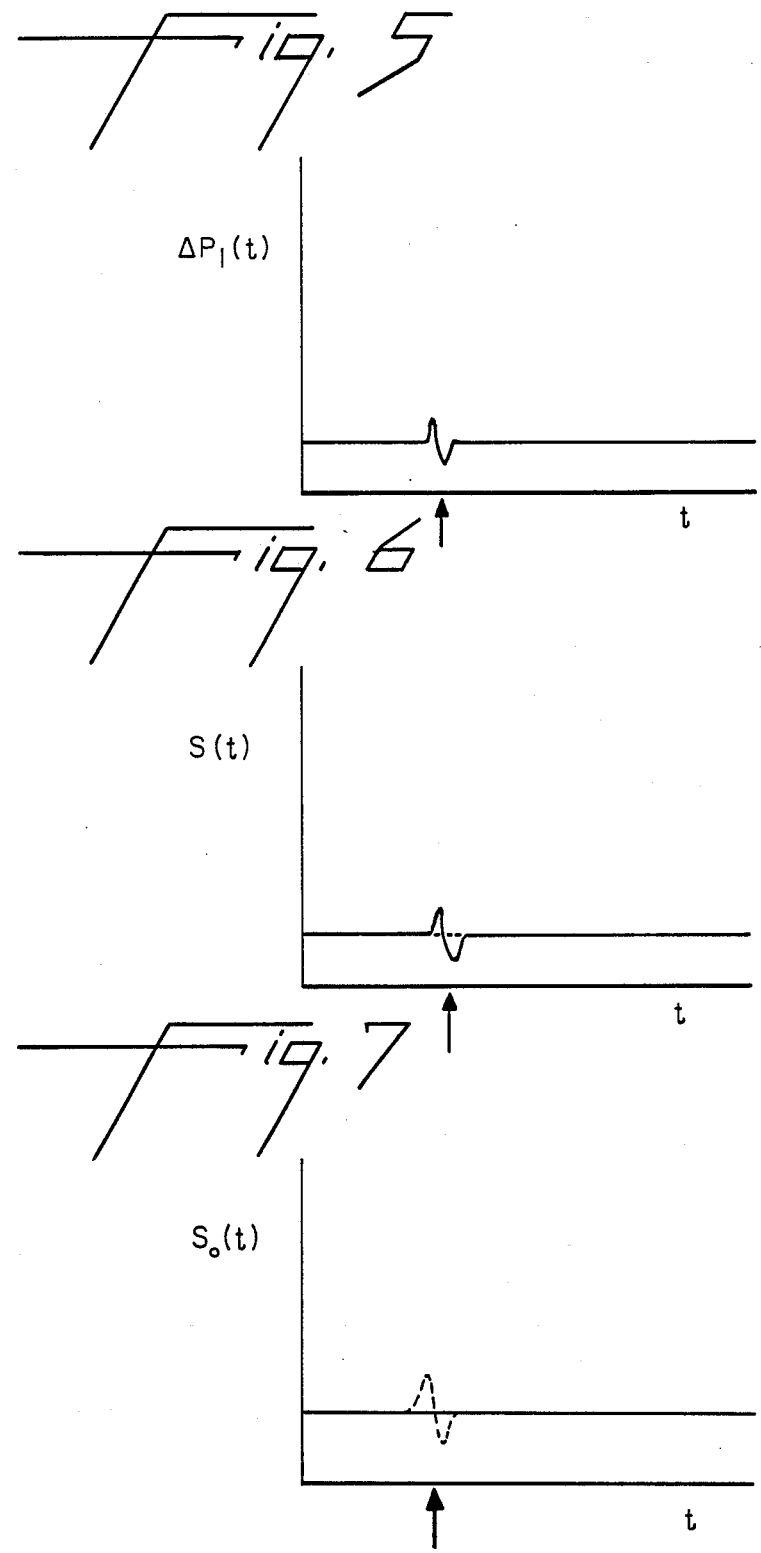

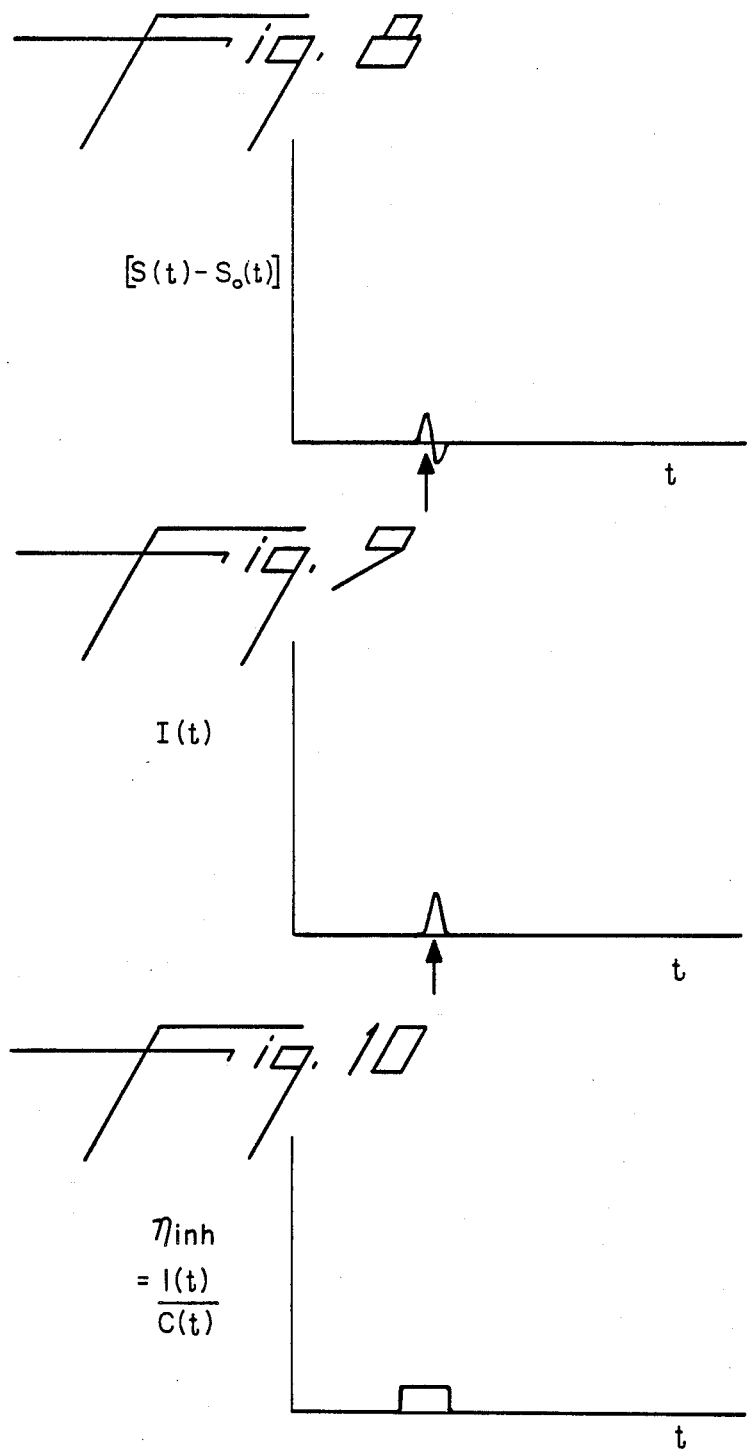

VISCOSITY DETECTION METHOD FOR LIQUID CHROMATOGRAPHY SYSTEMS WITH CARRIER LIQUIDS HAVING TIME-VARYING VISCOSITY

BACKGROUND OF THE INVENTION

U.S. Pat. No. 4,793,174 discloses a method for determining the intrinsic or inherent viscosity of a solute in solution with a solvent. In one embodiment, a gel permeation column separates a multicomponent sample into its separate solute components, each of which is subject to a separate viscosity determination.

In some applications, it may be desirable to separate a multicomponent sample into its separate solute components based on partitioning and chemical interaction, rather than molecular size. In such cases, the gel permeation column described in the above-identified application could be replaced, for example, with a column containing a packing material capable of binding each component of the multicomponent sample. The solvent flowing through the column could then be changed continuously with respect to some relevant chemical property, causing each component of the solute to elute sequentially under desired conditions of analysis time and experimental resolution. Under such circumstances, the viscosity of the solvent may, itself, vary from an initial to a final value, causing a varying "background" against which the solute viscosity is measured. It is an object of the present invention to provide a method for measuring the intrinsic or inherent viscosity of a solute in solution with such a solvent of varying viscosity.

SUMMARY OF THE INVENTION

The present invention provides a method for measuring the inherent viscosity of individual solute components in a multicomponent sample in solution with a solvent, comprising:

passing a stream of a carrier liquid having a viscosity which varies as a function of time at a flow rate R sequentially through (1) means for separating said sample into its individual solute components, (2) a first capillary tube and (3) a second capillary tube, which tubes are separated from each other by an offset volume $\Delta V$, where $0 < \Delta V \leq RT$, where T is as defined below;

introducing into said stream of carrier liquid, upstream of said means for separating said sample into its individual solute components, a predetermined volume of a solution comprising the sample and the solvent, whereby said sample is separated into its individual solute components;

measuring, as a function of time, pressure differences $\Delta P_1(t)$ and $\Delta P_2(t)$ across said first and second capillary tubes, respectively, said $\Delta P_1(t)$ and $\Delta P_2(t)$ being characterized by a rise time T;

measuring, as a function of time, the concentration $C(t)$ of the individual solute components in the carrier liquid;

obtaining a function $S(t)$, where $$S(t) = \ln [\Delta P_1(t)/\Delta P_2(t)];$$

obtaining a function $S_o(t)$, where $$S_o(t) = \ln [\Delta P_1(t)/\Delta P_2(t)]$$

when only carrier liquid is flowing through both the first and second capillary tubes;

obtaining a function $I(t)$, where $$I(t) = \int [S(t) - S_o(t)] dt;$$

and relating $C(t)$, $I(t)$ and $\Delta V$ to the inherent viscosity of the individual solute components.

BRIEF DESCRIPTION OF THE DRAWINGS

FIG. 2 is a stylized plot showing viscosity, $\eta$, of carrier liquid as a function of time, FIG. 3 is a stylized plot of concentration, C, as a function of time, t, for the single solute component whose pressure difference effects are shown in FIG. 4.

FIG. 4 is a stylized plot of pressure differences $\Delta P_1$, and $\Delta P_2$ across first and second capillary tubes as functions of time, t, for a single solute component.

FIG. 5 is a stylized plot of $\Delta P_1 \Delta P_2$ as a function of time, t.

FIG. 6 is a stylized plot of the function S as a function of time, t.

FIG. 7 is a stylized plot of the function $S_o$ as a function of time, t.

FIG. 8 is a stylized plot of the function $[S - S_o]$ as a function of time, t.

FIG. 9 is a stylized plot of the function I as a function of time, t.

FIG. 10 is a stylized plot of inherent viscosity, $\eta_{inh}$, as a function of time, t.

DETAILED DESCRIPTION OF THE INVENTION

Figure 1:
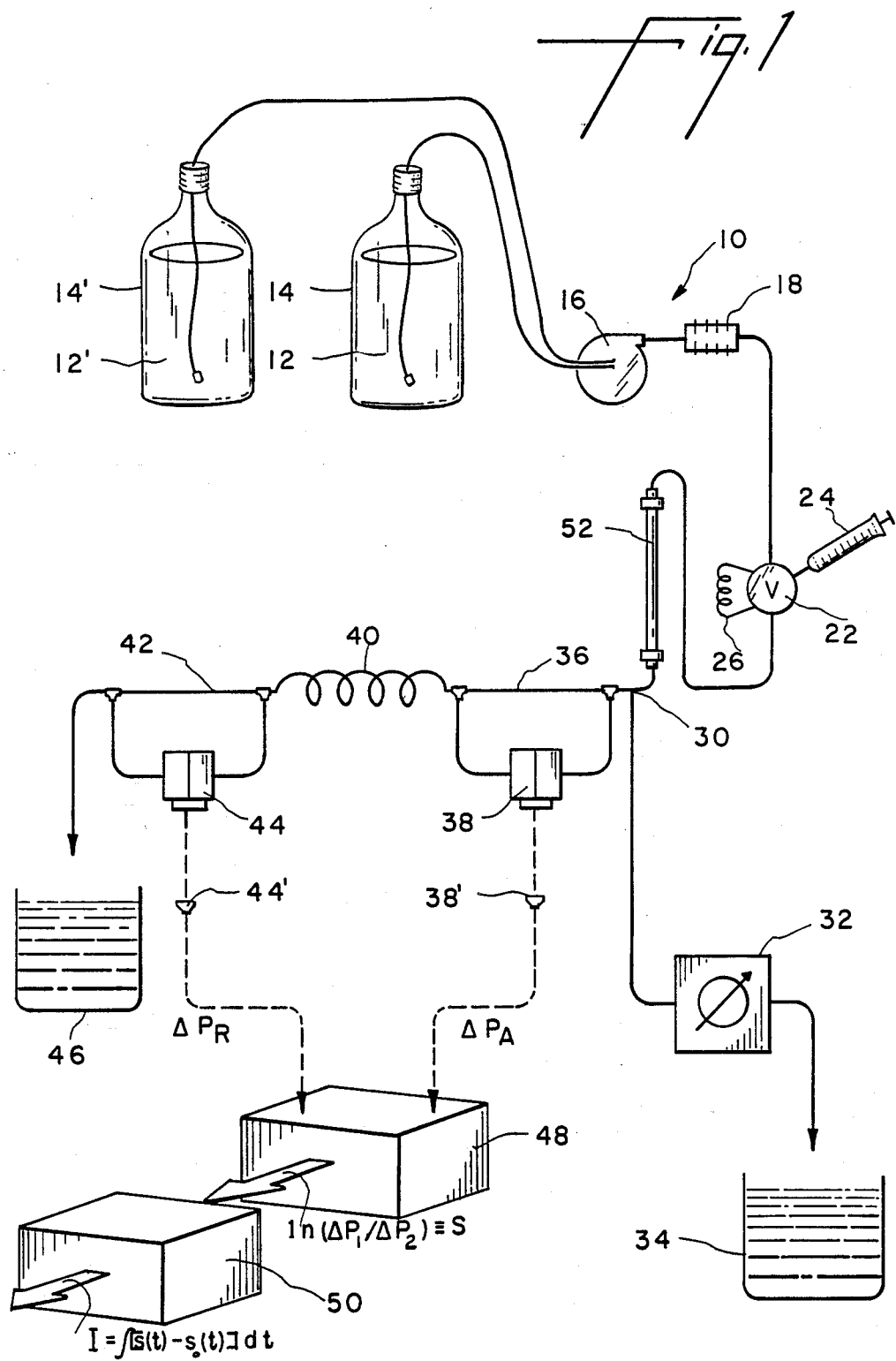
FIG. 1 is a stylized view of apparatus for carrying out the method of the present invention.

Referring now to the drawing, in which like reference numerals indicate like elements, there is seen in FIG. 1 an apparatus 10 in accordance with the present invention. Carrier liquids 12, 12' having viscosities $\eta_1$ and $\eta_2$, respectively, are pumped from reservoirs 14, 14' by a pump/mixer 16 through a pulse dampener 18 to a sample injection valve 22. The pump/mixer is set to mix the two carrier liquids 12, 12' at a predetermined rate. FIG. 2 depicts a plot showing viscosity of the mixed carrier liquid as a function of time. The plot shows a linear increase from a predetermined minimum to a predetermined maximum. Nonlinear functions may also be used. Referring again to FIG. 1, the pump/mixer 16 may be any type of pump/mixer which is used conventionally in liquid chromatography. An example of a suitable pump/mixer 16 is a Hewlett-Packard Model 1050. The dampener 18 is required only if a reciprocal piston-type pump is used. Typically, the dampener will be chosen to dampen high frequency pulses without impeding the overall flow rate of the mixed carrier liquids 12, 12'. The tubing utilized in the apparatus is not critical. Generally, any small internal diameter tubing which is substantially chemically inert with respect to the carrier liquids and solute may be utilized. Preferred tubings are made of stainless steel or Teflon ® (polytetrafluoroethylene), which is available from E. I. du Pont de Nemours and Company, Wilmington, Delaware.

The sample injection valve 22 may be a 2-position 6-port valve. A suitable valve is sold by Valco Instruments, Inc. (Houston, Texas) under the designation CV6UHPA.

Conveniently, a syringe 24, containing a multicomponent solute in solvent ("sample solution"), may be utilized to fill sample loop 26 with sample solution. The sample injection valve 22 will be set to "load" position, which allows the mixed carrier liquid 12, 12' to flow across the valve, while allowing sample loop 26 to be filled from syringe 24.

After sample loop 26 is filled with sample solution, valve 22 will be set to "inject" position, which diverts the flow of mixed carrier liquid 12, 12' to sample loop 26. The sample solution will then be introduced into the flowing stream of mixed carrier liquid 12, 12', as a substantially localized volume.

Alternatively, the sample solution may be injected directly into the flowing stream of mixed carrier liquid 12, 12'.

The stream of flowing mixed carrier liquid 12, 12' having a time varying viscosity and containing the multicomponent solute will pass through means for separating the multicomponent solute into its individual solute components. A preferred separating means is column 52 which may contain a packing material for which the individual solute components in the sample have varying affinities. Suitable packing materials include Zorbax ®—ODS. Other suitable separating means include Zorbax ® C-8 columns; both are commercial products from E. I. du Pont de Nemours and Company, Wilmington, Delaware.

After entering column 52, the individual solute components will elute one by one as the viscosity of the carrier liquid changes from a first value $\eta_A$ to a second value $\eta_B$. $\eta_A$ may be equal to $\eta_1$ or may equal some predetermined viscosity based on some initial composition using liquids 12 and 12'. Similarly, $\eta_B$ may be equal to $\eta_2$ or may equal some predetermined viscosity based on a final composition using liquids 12 and 12'. It should be understood that it is not necessarily the change in carrier liquid viscosity which causes sequential elution of the individual components, but rather the changing chemical and/or physical composition of the carrier liquid, which may, in turn, result in an unavoidable change in viscosity. It should also be understood that it is not necessary to change the chemical composition of carrier liquid for eluting solute components sequentially. Chromatographic separations using a carrier liquid of constant composition are called isocratic separations. Isocratic separations may often result in excessive analysis time and very uneven experimental resolution. These problems can sometimes be avoided by employing so-called temperature programming by which the temperature of the carrier liquid is changed with time, thereby resulting in a viscosity change with time.

The stream of flowing mixed carrier liquid 2, 12', now containing separated individual solute components, can be split at a junction 30, so that a portion of the stream passes through a concentration detector 32 into a waste receptacle 34 and another portion passes to first and second capillary tubes, discussed below. Alternatively, the concentration detector 32 can be placed in series with the capillary tubes 36 and 42, discussed below. The concentration detector 32 may be any type of detector which is typically used in liquid chromatography. A preferred concentration detector 32 is a differential refractometer. Other types of concentration detectors such as ultraviolet or infrared devices also may be used, depending upon the particular type of solute whose viscosity is being measured. FIG. 3 depicts the output of the concentration detector 32 as a function of time for an individual solute component.

Referring again to FIG. 1, the flowing mixed carrier liquid 12, 12'——containing separated individual solute components ——will pass through a first capillary tube 36, across which differences in pressure as a function of time will be detected by transducer 38. The carrier liquid will continue to flow through an offset volume element 40 into a second capillary tube 42, across which differences in pressure as a function of time will be detected by transducer 44. Finally, the carrier liquid will be emptied into a waste receptacle 46.

The internal diameter of the capillary tubes 36, 42 is not critical. Generally, the internal diameter will be chosen to maximize the performance of the pressure transducers associated with each capillary tube. Generally, the internal diameter will be larger than 7 mil. It is preferred that capillary tubes 36 and 42 be as close to physically identical as possible.

The pressure transducers can be the well-known diaphragm type such as those manufactured by Celesco Transducers Products, Inc. (Conoga Park, California). Typically, the transducers 38, 44 are connected across their respective capillary tubes 36, 42 by means of "T" connectors. Each pressure transducer 38, 44 is connected to its own amplification means 38', 44', respectively, with variable gain control. Preferably the amplification means comprises a DC amplifier. The variable gain controls are used to control the magnitude of the outputs from the two pressure transducers. Specifically, the two gains will be adjusted to provide equal outputs when the same carrier liquid is flowing through capillary tubes 36 and 42. FIG. 4 depicts the pressure changes across capillary tubes 36, 42 as a function of time. It should be noted that the curves are identical except for a time offset.

Advantageously, the fluid circuit defined by the apparatus 10 will be placed in a bath (not shown) at a preselected temperature. The bath will help to minimize temperature gradients within the apparatus.

Referring again to FIG. 1, the outputs from transducers 38 and 44 can be applied to the inputs (not shown) of a differential logarithmic amplifier 48. A suitable amplifier is a Burr Brown Log 100 JP. The output signal of the differential logarithmic amplifier 48 can be expressed by the following equation:

$$S(t) = \ln [\Delta P_1(t)/\Delta P_2(t)]$$

This output is a function of time. The output S(t) is then integrated over time.

The apparatus depicted in FIG. 1 allows a stream of carrier liquid containing individual solute components to pass sequentially through two capillary tubes separated by a small offset volume. As each component passes through each capillary tube, the pressure difference across the tube will rise from a baseline to a maximum value in a characteristic rise time (T). As each component leaves each capillary tube, the pressure difference across the tube will decay back to baseline in a characteristic decay time, which should approximate the rise time. After each component has passed through both capillary tubes, the respective pressure transducers will have generated two substantially identical pressure versus time curves, which curves are separated from one another by a time difference, $\Delta T$, which is equal to the offset volume $\Delta V$ divided by the flow rate R. When $\Delta T$ is sufficiently small, the two pressure versus time curves will be slightly displaced from one another, thereby allowing one curve to be used to approximate a value on the other curve. Generally, this condition will be achieved when the offset volume $\Delta V$ lies between 0 and RT.

To compensate for the contribution of $\Delta P_1(t)$ and $\Delta P_2(t)$ which is caused not by the individual solute component, but by the change in viscosity of the mixed carrier liquid 12, 12', it is necessary to determine a function $S_o(t)$ which reflects only the contribution of the mixed carrier liquid 12, 12' to $\Delta P_1(t)$ and $\Delta P_2(t)$. A convenient way to determine this function is to extrapolate the baseline of the S(t) curve through any sinusoidal responses. The resulting curve will represent $S_o(t)$. FIG. 7 depicts the result of such an extrapolation. The sinusoidal response of the solute is shown in dotted lines. The solid line represents the function $S_o(t)$.

To calculate inherent viscosity, a new function $[S(t) - S_o(t)]$ is formed. This function essentially subtracts the mixed carrier liquid 12, 12' baseline from the S(t) curve. FIG. 8 depicts this new function, in which the sinusoidal response has been lowered to the baseline.

Next a function I(t) is obtained:

$$I(t) = \int [S(t) - S_o(t)] dt.$$

Such a function is depicted in FIG. 9. Finally, for each individual solute component, the function I(t) is divided by C(t) for that component. The height of the resulting curve represents inherent viscosity. The integration comprising for each component (1) measuring pressure differences for solvent and for solvent with solute component, as a function of time across two capillary tubes in fluid communication (2) measuring concentrations of component as a function of time, and (3) obtaining inherent viscosity by means of a described mathematical relationship can be done by well-known manual computational methods or by an electronic integrator or digital computer.

WHAT IS CLAIMED:

1. A method for measuring the inherent viscosity of individual solute components in a multicomponent sample in solution with a solvent, comprising:

passing a stream of a carrier liquid having a viscosity which varies as a function of time at a flow rate R sequentially through (1) means for separating said sample into its individual solute components, (2) a first capillary tube and (3) a second capillary tube, which tubes are separated from each other by an offset volume $\Delta V$, where $0 < \Delta V \leq RT$, where T is as defined below;

introducing into said stream of carrier liquid, upstream of said means for separating said sample into its individual solute components, a predetermined volume of a solution comprising the sample and the solvent, whereby said sample is separated into its individual solute components;

measuring, as a function of time, pressure differences $\Delta P_1(t)$ and $\Delta P_2(t)$ across said first and second Capillary tubes, respectively, said $\Delta P_1(t)$ and $\Delta P_2(t)$ being characterized by a rise time T;

measuring, as a function of time, the concentration C(t) of the individual solute components in the carrier liquid;

obtaining a function S(t), where $$S(t) = \ln [\Delta P_1(t)/\Delta P_2(t)];$$

obtaining a function $S_o(t)$, where $$S_o(t) = \ln [\Delta P_1(t)/\Delta P_2(t)]$$

when only carrier liquid is flowing through both the first and second capillary tubes;

obtaining a function I(t), where $$I(t) = \int [S(t) - S_o(t)] dt;$$

and relating C(t), I(t) and $\Delta V$ to the inherent viscosity of the individual solute components.

* * * * *